(12) United States Patent
Mueller et al.

(10) Patent No.: US 12,389,522 B2
(45) Date of Patent: Aug. 12, 2025

(54) LINEAR ACCELERATOR SYSTEM HAVING A MAGNET UNIT FOR ELECTRON BEAM DEFLECTION

(71) Applicant: Siemens Healthcare GmbH, Erlangen (DE)

(72) Inventors: Sven Mueller, Urbich (DE); Stefan Willing, Rudolstadt (DE); Martin Koschmieder, Uhlstaedt-Kirchhasel (DE); Claudia Noak, Uhlstaedt-Kirchhasel (DE); Marvin Moeller, Jena (DE)

(73) Assignee: SIEMENS HEALTHINEERS AG, Fochheim (DE)

( * ) Notice: Subject to any disclaimer, the term of this patent is extended or adjusted under 35 U.S.C. 154(b) by 997 days.

(21) Appl. No.: 17/479,277

(22) Filed: Sep. 20, 2021

(65) Prior Publication Data

US 2022/0104339 A1    Mar. 31, 2022

(30) Foreign Application Priority Data

Sep. 28, 2020    (DE) ..................... 10 2020 212 200.8

(51) Int. Cl.
*H05H 7/04*    (2006.01)
*A61N 5/10*    (2006.01)
(Continued)

(52) U.S. Cl.
CPC ................ *H05H 7/04* (2013.01); *A61N 5/10* (2013.01); *G21K 5/04* (2013.01); *H05H 9/00* (2013.01);
(Continued)

(58) Field of Classification Search
USPC .................................................. 250/396 ML
See application file for complete search history.

(56) References Cited

U.S. PATENT DOCUMENTS 4,293,772 A    10/1981   Stieber
6,052,435 A    4/2000    Hernandez-Guerra et al.
(Continued)

FOREIGN PATENT DOCUMENTS

CN    101163371 A    4/2008
CN    102647849 A    8/2012
(Continued)

OTHER PUBLICATIONS

German Office Action mailed Jun. 1, 2021.
Gu Hongchun et al:"Progress on Radiation Processing by Electron Beam", Nuclear Physics Review, Nr. 03, 30. Sep. 1997.

*Primary Examiner* — Kiet T Nguyen
(74) *Attorney, Agent, or Firm* — Harness, Dickey & Pierce, P.L.C.

(57) ABSTRACT

A linear accelerator system according to an embodiment is for generating an MeV electron beam. The linear accelerator system includes a linear accelerator cavity having an enclosure, wherein the enclosure is open at one end to provide an exit port for the MeV electron beam; and a switchable magnet unit designed to, in a deflection mode, generate a magnetic field within the linear accelerator cavity to enable at least one electron, emitted within the linear accelerator cavity, to interact with the enclosure due to deflection away from the exit port caused by the magnetic field. Accordingly, in an embodiment, in the deflection mode, an intensity of the MeV electron beam passing through the exit port is relatively lower than an intensity of the MeV electron beam passing through the exit port in a beam generation mode of the switchable magnet unit.

22 Claims, 5 Drawing Sheets

(51) Int. Cl.
*G21K 5/04* (2006.01)
*H05H 9/00* (2006.01)

(52) U.S. Cl.
CPC .............. *A61N 2005/1089* (2013.01); *H05H 2007/046* (2013.01)

(56) References Cited

U.S. PATENT DOCUMENTS

| | | |
|---|---|---|
| 2004/0213375 A1 | 10/2004 | Bjorkholm et al. |
| 2008/0198970 A1 | 8/2008 | Kirshner et al. |
| 2009/0289194 A1 | 11/2009 | Saito |
| 2010/0002843 A1 | 1/2010 | Liu et al. |
| 2010/0039051 A1 | 2/2010 | Clayton et al. |
| 2011/0188638 A1 | 8/2011 | Treas et al. |
| 2016/0147161 A1* | 5/2016 | Nikipelov ............. H01S 3/0903 355/67 |
| 2024/0090112 A1* | 3/2024 | Agustsson ............... G21K 5/10 |

FOREIGN PATENT DOCUMENTS

| | | |
|---|---|---|
| CN | 105636331 A | 6/2016 |
| DE | 102012212720 A1 | 1/2014 |
| EP | 0037051 B1 | 1/1985 |
| JP | H0555000 A | 3/1993 |
| JP | H05290999 A | 11/1993 |
| JP | H065396 A | 1/1994 |
| JP | H11186000 A | 7/1999 |
| JP | 2009009892 A | 1/2009 |
| JP | 2009205884 A | 9/2009 |

\* cited by examiner

LINEAR ACCELERATOR SYSTEM HAVING A MAGNET UNIT FOR ELECTRON BEAM DEFLECTION

PRIORITY STATEMENT

The present application hereby claims priority under 35 U.S.C. § 119 to German patent application number DE102020212200.8 filed Sep. 28, 2020, the entire contents of which are hereby incorporated herein by reference.

FIELD

Example embodiments of the invention generally relate to a linear accelerator system, an MeV beam device, a method for generating an MeV electron beam, and an associated computer program product.

BACKGROUND

A linear accelerator system is a well-known system for accelerating charged particles, particularly electrons, along a straight line. Depending on the type of linear accelerator system, the electrons are accelerated to energies in excess of 1 MeV, in particular via a radiofrequency source, in a linear accelerator cavity. The accelerated MeV electron beam can be used for various applications, such as patient therapy directly using the MeV electron beam or therapy after generation of MeV radiation by way of the MeV electron beam on a target. An alternative application of the MeV electron beam or MeV radiation relates in particular to non-destructive materials testing and/or fluoroscopic imaging of an object during a security check or customs inspection. Depending on the application, radiation protection requirements may be involved. As a rule, the MeV electron beam or MeV radiation intensity must therefore be reduced to a minimum. This intensity is termed in particular the dose.

The intensity of the MeV electron beam or the MeV radiation typically varies at the start of electron injection until a steady state is established. In other words, the intensity gradually increases until the linear accelerator system can provide a constant intensity under steady state conditions. In terms of radiation protection requirements, an initial intensity variation of this kind is disadvantageous. A time lag of this kind at start-up of the linear accelerator system can be caused in particular by the radiofrequency source needing to be resonantly tuned to a resonant frequency of the linear accelerator cavity. The time lag can be, for example, 100 ms or longer.

US 2010/0039051 A1 describes a regulation of a radiofrequency power of a radiofrequency source operated in steady state via a reflection phase shifter device which can vary the RF power comparatively quickly.

U.S. Pat. No. 6,052,435 A, for example, discloses the operation of a linear accelerator system, in particular a particle source and a radiofrequency source, under permanently steady state conditions, wherein, during the required MeV particle beam generation, the particle source and the radiofrequency source are operated simultaneously (synchronously) and, to reduce the MeV particle beam generation, the particle source and the radiofrequency source are operated in a time-offset manner.

SUMMARY

Embodiments of the invention provide a linear accelerator system, an MeV radiation device, a method for generating an MeV electron beam and an associated computer program product, wherein MeV electron beam generation can be reduced independently of electron source injection.

Advantageous embodiments are described in the claims.

The linear accelerator system according to at least one embodiment of the invention for generating an MeV electron beam comprises:
- a linear accelerator cavity having an enclosure, wherein the enclosure is open at one end to provide an exit port for the MeV electron beam; and
- a switchable magnet unit which, in deflection mode, is designed to generate a magnetic field within the linear accelerator cavity such that at least one electron emitted within the linear accelerator cavity interacts with the enclosure due to deflection away from the exit port by the magnetic field, so that, in deflection mode, an intensity of the MeV electron beam passing through the exit port is less than an intensity of the MeV electron beam passing through the exit port in beam generation mode of the magnet unit.

An MeV radiation device according to at least one embodiment of the invention comprises
- the linear accelerator system of an embodiment; and
- a target disposed in the region of the exit port for generating MeV radiation in response to an incident MeV electron beam.

A method according to an embodiment of the invention for generating an MeV electron beam comprises:
- providing the linear accelerator system or the MeV radiation device,
- switching the switchable magnet unit to deflection mode at a deflection time via a control unit,
- operating the radiofrequency source of the linear accelerator system in steady state,
- injecting electrons as an electron beam into the linear accelerator cavity via the electron source at an injection time after the deflection time during steady state operation of the radiofrequency source, and
- switching the switchable magnet unit to beam generation mode before, at, or after the injection time, wherein the MeV electro beam is generated.

The computer program product of at least one embodiment can be a computer program or comprise a computer program. In particular, the computer program product has program code segments that reproduce the method steps according to at least one embodiment of the invention. As a result, the method according to at least one embodiment of the invention can be carried out in a defined and repeatable manner, and control can be exercised over dissemination of the method according to at least one embodiment of the invention.

The computer program product is preferably configured such that the computing unit can execute the method steps according to at least one embodiment of the invention via the computer program product. In particular, the program code segments can be loaded into a memory of the computing unit and typically executed via a processor of the computing unit having access to the memory. When the computer program product, in particular the program code segments, is executed in the computing unit, typically all the embodiments of the described method according to the invention can be carried out.

The computer program product is stored, for example, on a physical computer-readable medium and/or stored digitally as a data package in a computer network. The computer program product can be the physical, computer-readable medium and/or the data package in the computer network.

Thus, at least one embodiment of the invention can also proceed from the physical computer-readable medium and/or the data package in the computer network.

At least one embodiment of the invention is directed to a linear accelerator system for generating an MeV electron beam, comprising:
- a linear accelerator cavity including an enclosure, the enclosure being open at one end to provide an exit port for the MeV electron beam; and
- a switchable magnet unit to, in deflection mode, generate a magnetic field within the linear accelerator cavity to enable at least one electron, emitted within the linear accelerator cavity, to interact with the enclosure due to deflection away from the exit port caused by the magnetic field, such that, in deflection mode, an intensity of the MeV electron beam passing through the exit port is relatively lower than an intensity of the MeV electron beam passing through the exit port in a beam generation mode of the switchable magnet unit.

At least one embodiment of the invention is directed to an MeV radiation device, comprising:
- the linear accelerator system of claim 1; and
- a target disposed in the region of the exit port for generating MeV radiation in response to an incident MeV electron beam.

At least one embodiment of the invention is directed to a method for generating an MeV electron beam, comprising:
- switching a switchable magnet unit of a linear accelerator system to a deflection mode at a deflection time via a controller;
- operating a radiofrequency source of the linear accelerator system in steady state;
- injecting electrons into a linear accelerator cavity of the linear accelerator system as an electron beam, via an electron source, at an injection time after the deflection time during steady state of the radiofrequency source; and
- switching the switchable magnet unit to beam generation mode before, at or after the injection time, wherein the electron beam is generated.

At least one embodiment of the invention is directed to a non-transitory computer program product, directly loadable into a memory of a computing unit, storing program code for carrying out the method of an embodiment when the program code is executed in the computing unit.

BRIEF DESCRIPTION OF THE DRAWINGS

The invention will now be described and explained in more detail with reference to the embodiments illustrated in the figures. In the following description of the figures, structures and units that remain essentially the same are always designated by the same reference character as when the respective structure or unit first occurred.

DETAILED DESCRIPTION OF THE EXAMPLE EMBODIMENTS

Figure 1:
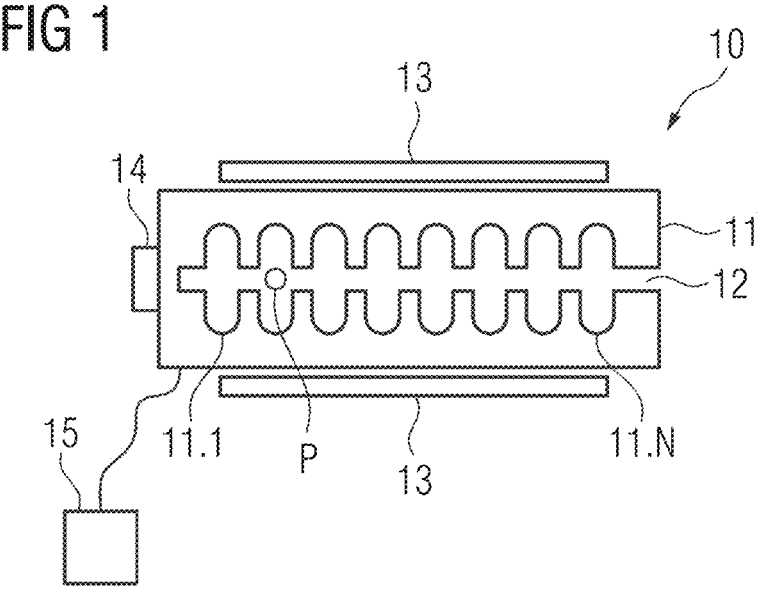
FIG. 1 shows a linear accelerator system for generating an MeV electron beam.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The linear accelerator system according to at least one embodiment of the invention for generating an MeV electron beam comprises:
- a linear accelerator cavity having an enclosure, wherein the enclosure is open at one end to provide an exit port for the MeV electron beam; and
- a switchable magnet unit which, in deflection mode, is designed to generate a magnetic field within the linear accelerator cavity such that at least one electron emitted within the linear accelerator cavity interacts with the enclosure due to deflection away from the exit port by the magnetic field, so that, in deflection mode, an intensity of the MeV electron beam passing through the exit port is less than an intensity of the MeV electron beam passing through the exit port in beam generation mode of the magnet unit.

The linear accelerator system may be designed in particular for therapy, materials testing and/or security inspection. The linear accelerator system typically has a radiofrequency source for accelerating the at least one electron to a predeterminable MeV energy in the direction of the exit port. During beam generation mode and/or deflection mode, the radiofrequency source is typically in steady state. For example, the predeterminable MeV energy can be as much as 9 MeV or in the range of 1 to 6 MeV. The linear accelerator system is particularly advantageous because free electrons are emitted regularly inside the linear accelerator cavity by a field effect emission on the enclosure. In particular, the electron beam can comprise electrons injected via an electron source and emitted via the field effect, which electrons can be inventively deflected before passing through the exit port. In particular, the field effect emission occurs on a cold surface of the enclosure. In addition, the field effect emission depends on a radiofrequency power applied via a radiofrequency source and/or an age of the accelerator cavity and/or a degree of contamination of the accelerator cavity.

The radiofrequency source is conventionally operated under steady state conditions, so that during this period the typically maximum radiofrequency power is applied to the linear accelerator cavity, causing in particular the free electrons to be generated via the field effect. The proportion of the electrons emitted by field effect can be up to 1% of the intensity of the MeV electron beam. For example, at a maximum MeV electron beam energy of 6 MeV, an intensity of the injected electrons is 2 Gy/min at approx. 100 mA injection current and an intensity of the free electrons emitted by field effect is 1-10 mGy/min.

The magnet unit allows advantageous regulation of the intensity of the MeV electron beam passing through the exit port via repeatable switching from deflection mode to beam generation mode and back. In particular, the regulation comprises decreasing and increasing the intensity. In particular, regulation is performed by time-variant deflection of the at least one electron emitted within the linear accelerator cavity. The magnetic field strength of the magnet unit can be up to 2 T, in particular up to 1 T, for example.

The MeV electron beam can preferably be generated with stepped intensities, in particular in a binary manner, for example with full intensity or with a lower partial intensity. In particular, the lower partial intensity can be zero. Intermediate steps between full intensity and low partial intensity are advantageously avoided. The MeV electron beam is advantageously generated with only two different predetermined intensity levels. A turn-on time, which describes a period from partial intensity, in particular from zero intensity, to full intensity, is advantageously less than 1 ms.

The intensity of the MeV electron beam can preferably be reduced when the magnet unit is operating in deflection mode such that, for example, a user of the linear accelerator system can be within a radiation zone of the linear accelerator system in compliance with radiation protection requirements. The radiation zone is typically in the vicinity of the exit port of the linear accelerator cavity. Depending on the application of the linear accelerator system, the radiation zone can be an examination area for materials testing, security inspection, customs check, and/or medical imaging, or an irradiation zone for therapy. A safety level of the linear accelerator system is thus advantageously increased.

With regard to a conventional linear accelerator system having an adjustable aperture in front of the exit port for particle absorption, in particular for electron absorption, another advantage can be that, because of the interaction according to the invention, in particular the absorption within the linear accelerator cavity, an energy of the particles to be absorbed is reduced. This is in particular because, for absorption, the MeV electron beam interacts not only after complete acceleration in the accelerator cavity, but advantageously immediately after field effect emission and/or after electron injection. Heat generation in the linear accelerator cavity can be reduced as a result. Advantageously, the magnet unit can switch between deflection mode and beam generation mode much faster compared to a conventional aperture.

In particular, the MeV electron beam comprises a plurality of packets containing electrons. A packet can alternatively be referred to as a pulse. The MeV electron beam can therefore be a pulsed electron beam. A pulsed electron beam is regularly generated in so-called continuous wave mode of the linear accelerator system. In particular, a packet comprises the electrons injected at a point in time over a short duration by the electron source. A pulse frequency denotes, in particular, the regularity of the injection of electrons by the electron source. The pulse frequency can be higher than or equal to 100 Hz. In principle, the pulse frequency can be up to 1000 Hz or alternatively less than 100 Hz. Typically, the radiofrequency source also exhibits the pulse frequency under steady state conditions, so that the radiofrequency source and the electron source are synchronized.

In one embodiment, the linear accelerator system has an electron source for injecting electrons as an electron beam into the linear accelerator cavity, wherein the electron source is designed to inject fewer electrons when the magnet unit is operating in deflection mode than when the magnet unit is operating in beam generation mode. This embodiment is particularly advantageous because it means that fewer electrons are deflected, in particular need to be deflected, when the magnet unit is operating in deflection mode in order to reduce the intensity of the MeV electron beam. In particular, as a result of the reduced intensity, the dose is also reduced. The dose is typically proportional to the accumulated energy of the MeV electron beam to the power of three. Loss of electrons due to interaction with the enclosure is regularly reduced, which can in particular result in reduced heat generation in the linear accelerator cavity. In particular, the cooling power and/or dimensions of a shielding device of the linear accelerator system can therefore be advantageously reduced. A control unit is usually designed to regulate the injection current, which includes the injected electrons, of the electron source.

One embodiment provides that no electrons are emitted via the electron source when the magnet unit is in deflection mode. A particular advantage of this embodiment is that, in deflection mode, only the electrons emitted by field effect emission are deflected. In particular, this means that the magnetic field strength can be reduced compared to an embodiment with electron injection. The dimensions of the magnet unit are advantageously reduced as a result. For example, the control unit can at times completely eliminate electron injection.

In one embodiment, the linear accelerator system has a clock unit which is designed to synchronously switch the switchable magnet unit and the electron source. By synchronously switching the switchable magnet unit and the electron source, the electron packets can advantageously be separated in such a way that no electrons are accelerated between the electron packets and/or pass through the exit port. At the start of electron injection, the switchable magnet unit is therefore synchronously switched to beam generation mode. After the respective electron packet injection, the switchable magnet unit is switched to deflection mode. This embodiment is particularly advantageous because in particular the switchable magnet unit enables the different electron packets to be separated. A packet profile of the electron packets can thus resemble a jump function. In other words, the profile is advantageously rectangular in shape.

In one embodiment, the linear accelerator system has a safety device which is designed to switch the switchable magnet unit such that an intensity of the MeV electron beam passing through the exit port is essentially reduced to zero within a switch-off time of 10 ms. For example, the safety device can switch the switchable magnet unit to deflection mode so that the intensity is reduced to essentially zero. The intensity of "essentially zero" typically corresponds to a residual intensity that is harmless in terms of radiation protection requirements or that cannot be detected by measurement. In particular, the safety device is designed to comply with radiation protection requirements. This embodiment is particularly advantageous because a radiation protection requirement may stipulate that, from one electron packet to the next electron packet, the intensity of the MeV electron beam is reduced to essentially zero. Shutdown of the MeV electron beam is advantageously accomplished by deflection of electrons within the accelerator cavity so that preferably all the electrons interact with the enclosure. For example, the safety device can additionally be designed to switch off the radiofrequency source and/or the electron source. In particular, the switchable magnet unit increases the safety level because, in addition to shutting down the radiofrequency source and/or the electron source, the magnet unit can be switched to deflection mode.

One embodiment provides that the switch-off time is equal to or less than 1 ms. This embodiment is particularly advantageous in terms of radiation protection requirements because it enables the MeV electron beam to be switched off more quickly.

The control unit can in particular comprise the clock unit and/or the safety device, and/or control the electron source and/or the magnet unit and/or the radiofrequency source.

According to one embodiment, the linear accelerator system has a shielding device for absorbing brake radiation generated by the interaction of the at least one deflected electron. The shielding device can in particular be made of lead and/or tungsten and/or copper. The shielding device can form the enclosure of the accelerator cavity or surround the accelerator cavity. This embodiment is advantageous in particular for preventing the electrons interacting with the enclosure and/or the brake radiation generated by the interaction of the at least one deflected electron from escaping from the linear accelerator cavity. Advantageously, the brake radiation is absorbed completely, at least according to radiation protection requirements. Alternatively or in addition, the at least one electron itself is absorbed in the shielding device.

One embodiment provides that, in deflection mode, the magnet unit generates a magnetic field having a field strength such that an electron emitted within a cell of the linear accelerator cavity interacts with a section of the enclosure within the same cell. Thus, the at least one electron advantageously does not leave the cell in which the at least one electron was previously emitted. This embodiment is particularly advantageous because, prior to the interaction, the deflected electron is accelerated less, thereby reducing heat generation and/or a dose, which is usually disproportionate to the acceleration energy.

In one embodiment, the linear accelerator system has a reflection phase shifter device and the radiofrequency source, the reflection phase shifter device being connected between the radiofrequency source and the linear accelerator cavity such that, when the magnet unit is operating in deflection mode, the radiofrequency power of the radiofrequency source can be reduced via the reflection phase shifter device compared to beam generation mode of the magnet unit. Advantageously, this embodiment enables the radiofrequency source to be operated under steady state conditions with the radiofrequency power still remaining controllable via the reflection phase shifter device. As a result, a proportion of the free electrons generated via the field effect and/or the radiofrequency power causing the electrons to be accelerated can be advantageously reduced.

An MeV radiation device according to at least one embodiment of the invention comprises
  the linear accelerator system of an embodiment; and
  a target disposed in the region of the exit port for generating MeV radiation in response to an incident MeV electron beam.

In an embodiment, the MeV radiation device may be particularly designed for therapy, materials testing and/or security inspection. An advantage of the MeV radiation device can be that, similarly to the regulation of the MeV electron beam, the MeV radiation can be regulated as a function of the switchable magnet unit. In particular, the MeV radiation is MeV photon radiation, typically MeV X-ray radiation. The MeV radiation is generated, for example, when the MeV electron beam is decelerated in the target. The target consists of, for example, tungsten and/or copper. The target is preferably disposed at the exit port such that the MeV electron beam is preferably completely incident on the target.

A method according to an embodiment of the invention for generating an MeV electron beam comprises:
  providing the linear accelerator system or the MeV radiation device,
  switching the switchable magnet unit to deflection mode at a deflection time via a control unit,
  operating the radiofrequency source of the linear accelerator system in steady state,
  injecting electrons as an electron beam into the linear accelerator cavity via the electron source at an injection time after the deflection time during steady state operation of the radiofrequency source, and
  switching the switchable magnet unit to beam generation mode before, at, or after the injection time, wherein the MeV electro beam is generated.

The switching of the switchable magnet unit before, at, or after the injection time can be asynchronous or synchronous with the switching of the electron source. For example, the switchable magnet unit can be switched to beam generation mode asynchronously up to 100 ms before or up to 100 ms after the injection time.

According to one embodiment, the switchable magnet unit is switched to beam generation mode synchronously with electron injection at the injection time.

One embodiment provides that the magnet unit is switched alternately between deflection mode and beam generation mode, and synchronously with the electron source. Advantageously, no packets of electrons are emitted from the electron source in deflection mode. Typically no MeV electron beam is generated during this process.

The computer program product of at least one embodiment can be a computer program or comprise a computer program. In particular, the computer program product has program code segments that reproduce the method steps according to at least one embodiment of the invention. As a result, the method according to at least one embodiment of the invention can be carried out in a defined and repeatable manner, and control can be exercised over dissemination of the method according to at least one embodiment of the invention.

The computer program product is preferably configured such that the computing unit can execute the method steps according to at least one embodiment of the invention via the computer program product. In particular, the program code segments can be loaded into a memory of the computing unit and typically executed via a processor of the computing unit having access to the memory. When the computer program product, in particular the program code segments, is executed in the computing unit, typically all the embodiments of the described method according to the invention can be carried out.

The computer program product is stored, for example, on a physical computer-readable medium and/or stored digitally as a data package in a computer network. The computer program product can be the physical, computer-readable medium and/or the data package in the computer network. Thus, at least one embodiment of the invention can also proceed from the physical computer-readable medium and/ or the data package in the computer network.

The physical, computer-readable medium can typically be directly connectable to the computing unit, for example by inserting the physical, computer-readable medium into a DVD drive or plugging the physical, computer-readable medium into a USB port, thereby giving the computing unit in particular read-access to the physical, computer-readable medium. The data package can preferably be retrieved from the computer network. The computer network can contain the computing unit or can be indirectly connected to the computing unit via a wide area network (WAN) or a (wireless) local area network (WLAN or LAN) connection. For example, the computer program product can be digitally stored on a cloud server at a storage location of the computer network, transferred to the computing unit via the WAN via the Internet and/or via the WLAN or LAN, in particular by calling up a download link that points to the storage location of the computer program product.

Alternatively or in addition, the computer program product can be designed to reproduce an analog, in particular logical, interconnection of the linear accelerator system. The analog circuitry can be part of the control unit. In particular, the computer program product can be used to program an analog circuit, in particular a logic unit, for example an FPGA or an integrated controller or a plurality of transistors. In particular, the linear accelerator system can comprise an analog circuit for ensuring that the MeV electron beam is generated subject to the conditions that a safety circuit of the linear accelerator system is closed and the magnet unit is in beam generation mode and the electron source is injecting electrons. In particular, the safety circuit transmits a beam enable signal from a user of the linear accelerator system. The safety circuit comprises, for example, two signal paths that redundantly transmit the beam enable signal when the MeV electron beam is to be generated. For example, if the safety circuit is open, the magnet unit is preferably in deflection mode or the magnet unit is automatically switched to deflection mode.

Features, advantages or alternative embodiments mentioned in the description of the device are equally applicable to the method and vice versa. In other words, claims relating to the method can be further developed using features of the device and vice versa. In particular, the device according to at least one embodiment of the invention can be used in the method.

FIG. 1 shows a schematic arrangement of a linear accelerator system 10 for generating an MeV electron beam.

The linear accelerator system 10 has a linear accelerator cavity 11 with an enclosure, wherein the enclosure is open at one end to provide an exit port 12 for the MeV electron beam. The exit port 12 can be an exit window and/or form the linear accelerator cavity 11 together with the enclosure. A cell of the linear accelerator cavity 11 is typically referred to as an accelerator element. In this example embodiment, the linear accelerator cavity 11 has a plurality of cells 11.1 . . . 11.N. A field effect emission can typically occur in any cell 11.1 . . . 11.N. In particular, the linear accelerator cavity 11 is a resonator, for example a standing wave accelerator or a traveling wave accelerator.

The linear accelerator system 10 has a switchable magnet unit 13. In deflection mode, the switchable magnet unit 13 is designed to generate a magnetic field within the linear accelerator cavity 11 such that at least one electron P emitted within the linear accelerator cavity 11 interacts with the enclosure due to magnetic field induced deflection away from the exit port 12 such that, in deflection mode, an intensity of the MeV electron beam passing through the exit port 12 is lower than an intensity of the MeV electron beam passing through the exit port 12 in beam generation mode of the magnet unit 13.

An MeV electron beam in beam generation mode typically contains a plurality of electrons, for example up to 1 A. The at least one electron P is typically injected from an electron source 14 and/or generated via the field effect. The electrons are typically injected via the electron source 14. The linear accelerator system 10 incorporates the electron source 14. In particular, the electron source 14 emits the at least one electron P into the linear accelerator cavity 11, typically at the side opposite the exit port 12. The electron source 14 in particular injects a plurality of electrons as an electron beam into the linear accelerator cavity 11, so that the injected electron beam becomes an MeV electron beam due to acceleration in the linear accelerator cavity 11. In particular, the electron source 14 has a thermionic emitter, for example a filament-type emitter or a spherical emitter, or a cold emitter, for example with carbon tubes or silicon. The electron source 14 can have a grid for regulating electron injection.

The magnet unit 13 can typically be operated in multiple operating modes, typically in deflection mode or in beam generation mode. In particular, a magnetic field strength of the magnet unit 13 can be continuously controllable according to the plurality of operating modes. Switching of the magnet unit 13 basically refers to switching from one operating mode of the magnet unit 13 to another operating mode of the magnet unit 13.

The magnet unit 13 can be designed such that the magnetic field is essentially perpendicular to a longitudinal axis of the linear accelerator cavity 11. The magnetic field advantageously deflects the at least one electron P in the direction of a ground plane. The magnet unit 13 can have a plurality of magnets which are, for example, electromagnets and/or permanent magnets. Generating the magnetic field in deflection mode comprises amplifying or reducing a total magnetic field acting within the linear accelerator cavity 11. The total magnetic field can comprise the magnetic field of the magnet unit 13 and another magnetic field of another magnet unit. It is provided that, in deflection mode, a strength of the magnetic field is higher than a magnetic field strength in beam generation mode. Alternatively, the magnet unit 13 can be designed to compensate another magnetic field, so that in this case the ratio of the magnetic field strengths between deflection mode and beam generation mode can be reversed.

In particular, switching the magnet unit 13 into deflection mode comprises operating the magnet unit 13 such that the at least one electron P is deflected within the linear accelerator cavity 11. The intensity of the MeV electron beam passing through the exit port 12 depends in particular on the magnetic field strength. The magnetic field strength correlates, at least partially, with a number of electrons interacting with the enclosure. In beam generation mode, a number of electrons interacting with the enclosure is preferably reduced, advantageously to zero.

Deflection mode can be used, in particular, when a patient's healthy tissue is located in the region of the MeV electron beam while the patient is undergoing treatment or, for example, during a customs inspection of a truck with a driver in the cab 22 (not shown in FIG. 1). In this case, the magnet unit 13 can preferably reduce the intensity of the MeV electron beam to a harmless level.

The linear accelerator system 10 has a radiofrequency source 15 for accelerating the at least one electron P to a predeterminable MeV energy in the direction of the exit port 12. The radiofrequency source 15 can be a magnetron or a klystron.

Figure 2:
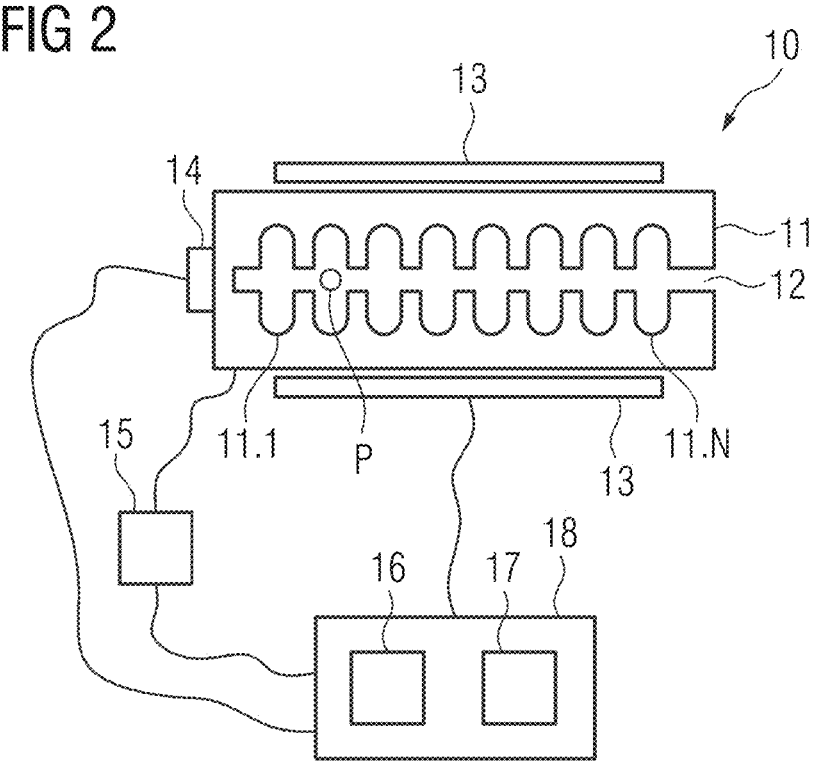
FIG. 2 shows the linear accelerator system in another embodiment.

FIG. 2 shows the linear accelerator system 10 in another embodiment.

The electron source 14 is designed to inject fewer electrons when the magnet unit 13 is operating in deflection mode than when the magnet unit 13 is operating in beam generation mode, in particular it is designed to inject no electrons.

The linear accelerator system 10 has a clock unit 16 which is designed to synchronously switch the switchable magnet unit 13 and the electron source 14, during which the radiofrequency source 15 is typically in steady state.

The linear accelerator system 10 has a safety device 17 which is designed to switch the switchable magnet unit 13 such that an intensity of the MeV electron beam passing through the exit port 12 is essentially reduced to zero within a switch-off time of 10 ms. In a preferred further embodiment, the switch-off time is equal to or less than 1 ms.

The linear accelerator system 10 has a control unit 18 which controls and/or synchronizes, in particular clocks, the magnet unit 13, the electron source 14 and the radiofrequency source 15. The control unit 18 can be reproduced in program code segments executable in a computing unit and/or connected to the magnet unit 13, the electron source 14 and/or the radiofrequency source 15 for control purposes.

In this embodiment, the control unit 18 additionally has the clock unit 16 and the safety device 17.

Figure 5:
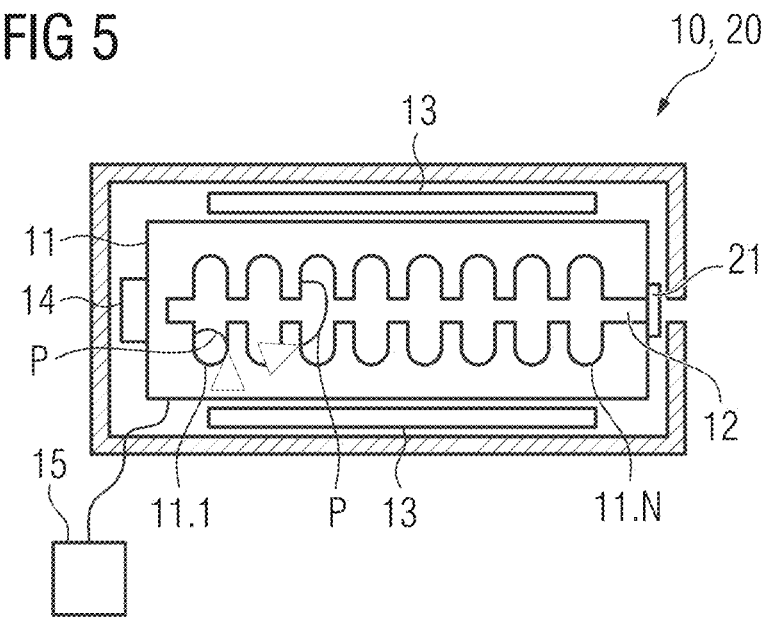
FIG. 5 shows an MeV beam device in deflection mode.

In a preferred further development of this embodiment as shown in FIG. 5, in deflection mode the magnet unit 13 generates a magnetic field having a field strength such that an electron emitted within a cell 11.1 . . . 11.N of the linear accelerator cavity 11 interacts with a part of the enclosure within the cell.

It is conceivable for the linear accelerator system 10 to additionally have a reflection phase shifter device (not shown in FIG. 2), wherein the reflection phase shifter device is connected between the radiofrequency source 15 and the linear accelerator cavity 11 such that, in deflection mode of the magnet unit 13, a radiofrequency power of the radiofrequency source 15 can be reduced via the reflection phase shifter device compared to beam generation mode of the magnet unit 13.

Figure 3:
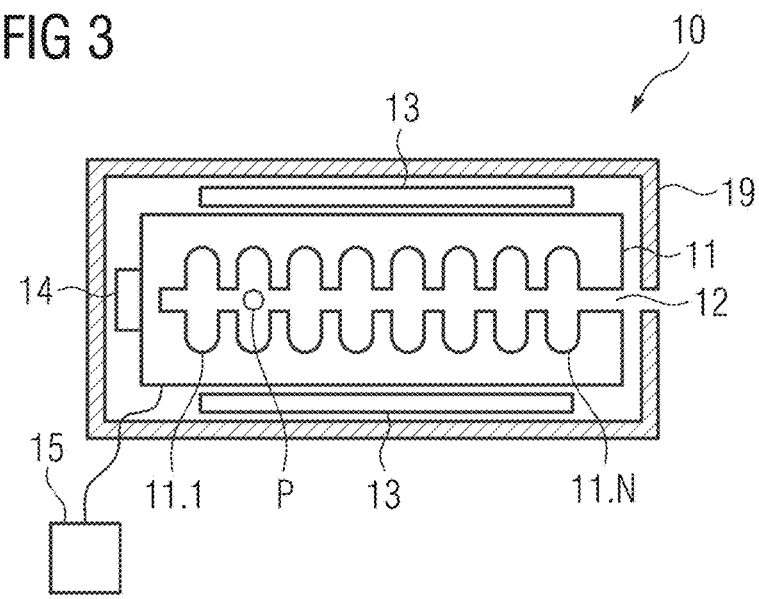
FIG. 3 shows the linear accelerator system in another embodiment.

FIG. 3 shows the linear accelerator system in an embodiment which is basically compatible with the embodiments shown in FIG. 1 and FIG. 2.

The linear accelerator system 10 has a shielding device 19 for absorbing brake radiation generated by the interaction of the at least one deflected electron. The shielding device 19 surrounds the enclosure of the linear accelerator cavity 11, but does not cover the exit port 12.

Figure 4:
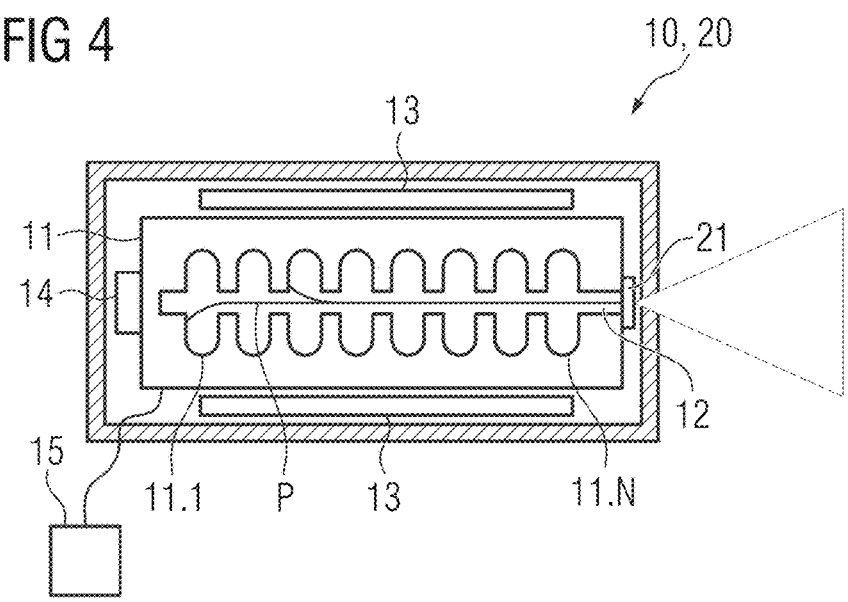
FIG. 4 shows an MeV beam device in beam generation mode.

FIG. 4 shows an MeV radiation device 20 in beam generation mode. The MeV radiation device has the linear accelerator system 10 designed according to one of the previous embodiments, and a target 21 disposed in the region of the exit port 12 for generating MeV radiation in response to an incident MeV electron beam. In this example embodiment, the shielding device 19 and at least one trajectory of the at least one electron P present in the linear accelerator cavity 11 are additionally shown.

FIG. 5 shows an MeV radiation device 20 in deflection mode, wherein the at least one electron P interacts with the enclosure of the linear accelerator cavity 11. FIG. 5 shows the embodiment wherein the electron emitted within the cell 11.1 . . . 11.N of the linear accelerator cavity 11 interacts with a part of the enclosure within the same cell.

Figure 6:
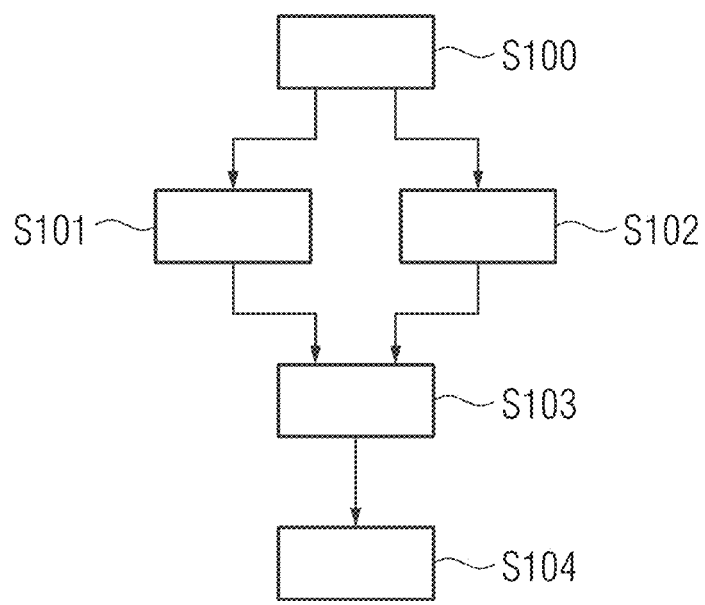
FIG. 6 shows a method for generating an MeV electron beam.

FIG. 6 shows a flowchart of a method for generating an MeV electron beam.

Method step S100 indicates providing a linear accelerator system 10 or an MeV radiation device 20. In particular, providing comprises preparing or scheduling operation of the linear accelerator system 10 or the MeV radiation device 20, typically immediately prior to a start-up of the linear accelerator system 10 or of the MeV radiation device 20 for electron beam or MeV radiation generation respectively.

Method step S101 denotes switching the switchable magnet unit 13 to deflection mode via a control unit 18 at a deflection time.

Method step S102 denotes operating the radiofrequency source 15 of the linear accelerator system 10 in steady state. In steady state, any necessary resonant tuning of the radiofrequency source 15 to a resonant frequency of the linear accelerator cavity 11 has preferably already been performed. A pulse frequency preferably corresponds to the resonant frequency.

Method step S103 denotes injecting electrons into the linear accelerator cavity 11 as an electron beam via the electron source 14 at an injection time after the deflection time during steady state of the radiofrequency source 15.

Method step S104 denotes switching of the switchable magnet unit 13 to beam generation mode before, at, or after the injection time, wherein the MeV electron beam is generated. Method step S104 can in particular be further developed such that the switchable magnet unit 13 is switched to beam generation mode synchronously with electron injection at the injection time.

In an advantageous further embodiment of this embodiment, the magnet unit 13 is switched alternately between deflection mode and beam generation mode and synchronously with the electron source 14.

Figure 7:
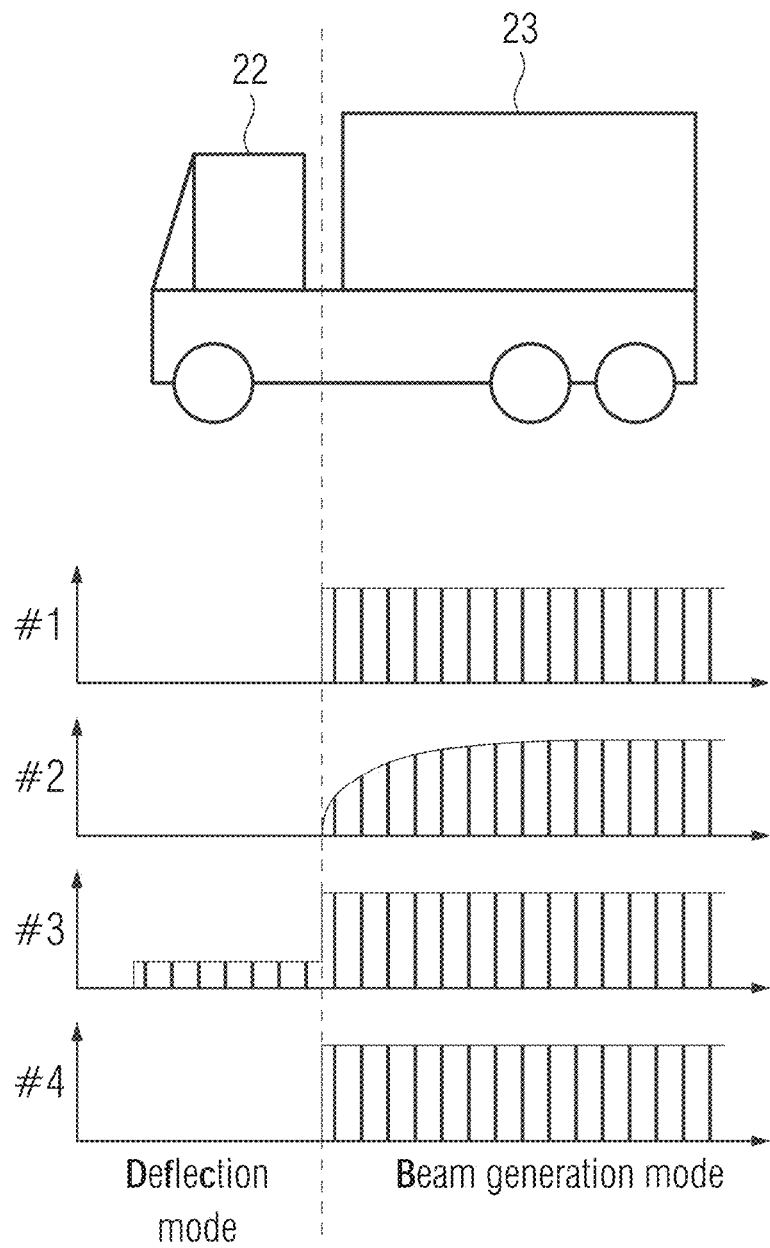
FIG. 7 shows a typical application for the linear accelerator system.

FIG. 7 shows a typical application for the linear accelerator system 10, in particular during a security inspection of a truck.

No MeV electron beam or no MeV radiation should be generated in the region of the driver's cab 22, for example zero intensity is required. In the region of the container 23, for example, an MeV electron beam is to be generated, advantageously with 100% intensity required, see intensity/time characteristic in line #1. Line #1 shows, for example, an ideal intensity/time characteristic, in particular one that complies with radiation protection requirements. For example, the 100% intensity specified can correspond to an acceleration energy of 9 MeV.

Line #2 shows the intensity/time characteristic according to the prior art with the intensity varying during start-up of the conventional linear accelerator system.

Line #3 shows the intensity/time characteristic according to another embodiment of the prior art using a conventional radiofrequency source in steady state without electron injection. It can be seen from this graph that an electron beam with reduced intensity is nevertheless generated in the region where zero intensity is required.

Line #4 shows the intensity/time characteristic according to the invention, in particular when the magnet unit is used in deflection mode and in beam generation mode. Advantageously, the intensity/time characteristic according to the invention has fewer deviations from the ideal intensity/time characteristic of line #1, in particular one that complies with radiation protection requirements.

Figure 8:
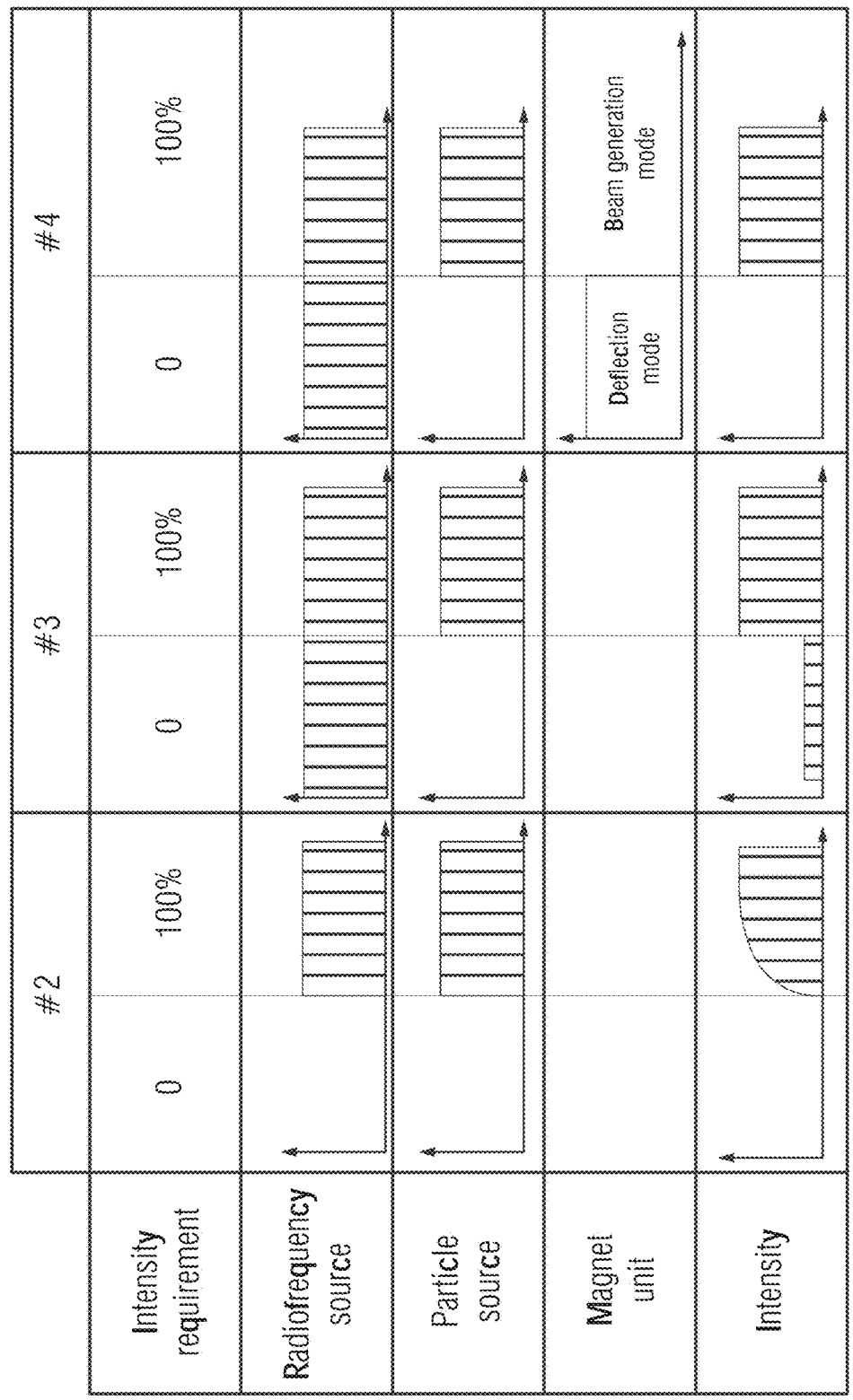
FIG. 8 shows an example comparison of the time-sequenced control of the linear accelerator system.

FIG. 8 shows an example comparison of the time-sequenced control of the linear accelerator system 10 according to lines #2, #3, #4 of FIG. 7.

In particular, line #4 illustrates the embodiment wherein the switchable magnet unit 13 is switched to beam generation mode synchronously with electron injection at the injection time. In this case, the magnet unit 13 switches from deflection mode to beam generation mode synchronously with the electron source 14.

Although the invention has been illustrated and described in detail by the preferred embodiments, the invention is not limited by the disclosed examples and other variations can be derived herefrom by the person skilled in the art without departing from the scope of protection of the invention.

Even if not explicitly stated, individual example embodiments, or individual sub-aspects or features of these example embodiments, can be combined with, or substituted for, one other, if this is practical and within the meaning of the invention, without departing from the present invention. Without being stated explicitly, advantages of the invention that are described with reference to one example embodiment also apply to other example embodiments, where transferable.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A linear accelerator system for generating an MeV electron beam, comprising:
   a linear accelerator cavity including an enclosure, the enclosure being open at one end to provide an exit port for the MeV electron beam; and
   a switchable magnet unit to, in deflection mode, generate a magnetic field within the linear accelerator cavity to enable at least one electron, emitted within the linear accelerator cavity, to interact with the enclosure due to deflection away from the exit port caused by the magnetic field, such that, in deflection mode, an intensity of the MeV electron beam passing through the exit port is relatively lower than an intensity of the MeV electron beam passing through the exit port in a beam generation mode of the switchable magnet unit.

2. The linear accelerator system of claim 1, further comprising:
   an electron source to inject electrons as an electron beam into the linear accelerator cavity, the electron source being designed to inject relatively fewer electrons in the deflection mode of the switchable magnet unit than in the beam generation mode of the switchable magnet unit.

3. The linear accelerator system of claim 2, wherein, in the deflection mode of the switchable magnet unit, no electrons are emitted via the electron source.

4. The linear accelerator system of claim 3, further comprising:
a clock unit designed to synchronously switch the switchable magnet unit and the electron source.

5. The linear accelerator system of claim 2, further comprising:
a clock unit designed to synchronously switch the switchable magnet unit and the electron source.

6. The linear accelerator system of claim 2, further comprising:
a safety device designed to switch the switchable magnet unit to essentially reduce an intensity of the MeV electron beam passing through the exit port to zero, within a switch-off time of 10 ms.

7. The linear accelerator system of claim 6, wherein the switch-off time is equal to or less than 1 ms.

8. The linear accelerator system of claim 2, further comprising:
a safety device designed to switch the switchable magnet unit to essentially reduce an intensity of the MeV electron beam passing through the exit port to zero, within a switch-off time of 10 ms.

9. The linear accelerator system of claim 8, wherein the switch-off time is equal to or less than 1 ms.

10. The linear accelerator system of claim 2, wherein the switchable magnet unit, in deflection mode, is configured to generate a magnetic field having a field strength to enable an electron emitted within a cell of the linear accelerator cavity to interact with a part of the enclosure within the cell.

11. The linear accelerator system of claim 2, further comprising:
a reflection phase shifter device and a radiofrequency source, wherein the reflection phase shifter device is connected between the radiofrequency source and the linear accelerator cavity such that, in deflection mode of the switchable magnet unit, a radiofrequency power of the radiofrequency source is reduceable via the reflection phase shifter device compared to beam generation mode of the switchable magnet unit.

12. The linear accelerator system of claim 1, further comprising:
a safety device designed to switch the switchable magnet unit to essentially reduce an intensity of the MeV electron beam passing through the exit port to zero, within a switch-off time of 10 ms.

13. The linear accelerator system of claim 12, wherein the switch-off time is equal to or less than 1 ms.

14. The linear accelerator system of claim 1, further comprising:
a shielding device for absorbing brake radiation generated by the interaction of the at least one deflected electron.

15. The linear accelerator system of claim 1, wherein the switchable magnet unit, in deflection mode, is configured to generate a magnetic field having a field strength to enable an electron emitted within a cell of the linear accelerator cavity to interact with a part of the enclosure within the cell.

16. The linear accelerator system of claim 1, further comprising:
a reflection phase shifter device and a radiofrequency source, wherein the reflection phase shifter device is connected between the radiofrequency source and the linear accelerator cavity such that, in deflection mode of the switchable magnet unit, a radiofrequency power of the radiofrequency source is reduceable via the reflection phase shifter device compared to beam generation mode of the switchable magnet unit.

17. An MeV radiation device, comprising:
the linear accelerator system of claim 1; and
a target disposed in a region of the exit port for generating MeV radiation in response to an incident MeV electron beam.

18. A method for generating an MeV electron beam, comprising:
switching a switchable magnet unit of a linear accelerator system to a deflection mode at a deflection time via a controller;
operating a radiofrequency source of the linear accelerator system in steady state;
injecting electrons into a linear accelerator cavity of the linear accelerator system as an electron beam, via an electron source, at an injection time after the deflection time during steady state of the radiofrequency source; and
switching the switchable magnet unit to beam generation mode before, at or after the injection time, wherein the electron beam is generated.

19. The method as claimed in claim 18, wherein the switching includes switching the switchable magnet unit to the beam generation mode synchronously with electron injection at the injection time.

20. The method of claim 19, wherein the switching includes alternately switching the switchable magnet unit between the deflection mode and the beam generation mode and in synchronism with the electron source.

21. The method of claim 18, wherein the switching includes alternately switching the switchable magnet unit between the deflection mode and the beam generation mode and in synchronism with the electron source.

22. A non-transitory computer program product, directly loadable into a memory of a computing unit, storing program code for carrying out the method of claim 18 when the program code is executed in the computing unit.

* * * * *